(12) United States Patent
Chen et al.

(10) Patent No.: US 12,702,763 B2
(45) Date of Patent: Aug. 11, 2026

(54) SHIELDING APPARATUS FOR LOWER END OF INJECTION NEEDLE AND INJECTION DEVICE

(71) Applicant: Zhejiang Kindly Medical Devices Co., Ltd., Wenzhou (CN)

(72) Inventors: Hong Chen, Wenzhou (CN); Xu Chen, Wenzhou (CN); Qian Zhang, Wenzhou (CN); Zhongshichao Chi, Wenzhou (CN); Zhuoyuan Lou, Wenzhou (CN)

(73) Assignee: Zhejiang Kindly Medical Devices Co., Ltd., Wenzhou (CN)

( * ) Notice: Subject to any disclaimer, the term of this patent is extended or adjusted under 35 U.S.C. 154(b) by 420 days.

(21) Appl. No.: 18/397,272

(22) Filed: Dec. 27, 2023

(65) Prior Publication Data

US 2024/0123158 A1 Apr. 18, 2024

(30) Foreign Application Priority Data

Sep. 8, 2023 (CN) ........................ 202311160460.6

(51) Int. Cl.
*A61M 5/32* (2006.01)

(52) U.S. Cl.
CPC ... *A61M 5/3245* (2013.01); *A61M 2005/3254* (2013.01)

(58) Field of Classification Search
CPC .................... A61M 5/3245; A61M 2005/3254
See application file for complete search history.

(56) References Cited

U.S. PATENT DOCUMENTS

| | | | | |
|---|---|---|---|---|
| 8,052,653 | B2 * | 11/2011 | Gratwohl .............. | A61M 5/326 604/164.08 |
| 8,801,673 | B2 * | 8/2014 | Zaiken ................ | A61M 5/3257 604/206 |
| 2005/0096603 | A1 | 5/2005 | Ooyauchi | |
| 2007/0244432 | A1 | 10/2007 | Shen et al. | |
| 2011/0160675 | A1 * | 6/2011 | Ruan .................. | A61M 5/3272 604/198 |
| 2013/0261559 | A1 | 10/2013 | Werbickas | |
| 2020/0069886 | A1 * | 3/2020 | Zhang ..................... | A61M 5/20 |

* cited by examiner

*Primary Examiner* — Phillip A Gray

(57) ABSTRACT

The present disclosure provides a shielding apparatus for a lower end of an injection needle and an injection device, and relates to the technical field of injection instruments. By using the shielding apparatus for a lower end of an injection needle in the present disclosure, in the process of mounting a needle holder on an insulin pen, and when the injection needle is completely removed from the insulin pen, the limit block also moves downwardly to abut against a bottom wall of the moving groove, and the shielding cylinder completely covers the lower end of the injection needle, so as to avoid a situation that a user accidentally touches the lower end of an injection needle to be injured, thereby avoiding the safety risk when the lower end of the injection needle is removed.

10 Claims, 3 Drawing Sheets

SHIELDING APPARATUS FOR LOWER END OF INJECTION NEEDLE AND INJECTION DEVICE

TECHNICAL FIELD

The present disclosure relates to the technical field of injection instruments, and in particular to a shielding apparatus for a lower end of an injection needle and an injection device.

BACKGROUND

Diabetes mellitus is trending towards epidemic and becoming an increasing global hazard. Currently, controlling the blood glucose level of diabetic patients is mainly achieved through insulin injections. The injection of insulin is achieved by means of a dedicated injection instrument, on which an injection needle is mounted. An upper end of the injection needle is used for the output of liquid medicine, while a lower end of the injection needle is used for the input of liquid medicine.

Therefore, to enable the injection needle to stably input the liquid medicine, the lower end of the injection needle is relatively sharp and can be pierced into a pre-filled vial of the injection instrument. However, the relatively sharp lower end, while satisfying the need for piercing of the injection needle, also brings about safety hazards for the removal of the injection needle, and the sharp lower end is prone to injure the user.

SUMMARY

An object of the present disclosure is to solve the problem of how to avoid the safety risk when a lower end of an injection needle is removed.

To solve the above problem, in an aspect, the present disclosure provides a shielding apparatus for a lower end of an injection needle, including:

a needle holder, used for mounting of an injection needle of an injection device and mounted on an insulin pen of the injection device, where the needle holder is provided with a moving groove, a limit groove and a first guiding bevel on an inner wall, the moving groove extending along an axial direction of the needle holder, the limit groove being located on a side of an upper end of the moving groove and being communicated with the moving groove through the first guiding bevel, and an end of the first guiding bevel connected to the limit groove being higher than an end of the first guiding bevel connected to the moving groove; and a shielding cylinder, mounted in the needle holder and allowing the injection needle to penetrate through, where a limit block for placing in the limit groove is provided on a side wall of the shielding cylinder, the limit block being placed below the first guiding bevel; when the needle holder is mounted on the insulin pen, the shielding cylinder abuts against the insulin pen and moves upwardly to allow the limit block in the limit groove to enter the moving groove along the first guiding bevel; and after the needle holder is separated from the insulin pen, the limit block moves downwardly along the moving groove to allow the shielding cylinder to cover and shield the lower end of the injection needle.

Compared with the prior art, the shielding apparatus for a lower end of an injection needle in the present disclosure has the following beneficial effects: a needle holder is provided as a mounting structure for an injection needle of an injection device, and the needle holder can be mounted on an insulin pen, such that the lower end of the injection needle can pierce into a pre-filled vial of the insulin pen, which facilitates the completion of the injection of liquid medicine by means of the injection needle. Moreover, a shielding cylinder is mounted in the needle holder, which allows the injection needle to penetrate through, so as to avoid interference caused by the mounting and normal use of the injection needle. On this basis, a limit groove is provided on an inner wall of the needle holder, a limit block is provided on a side wall of the shielding cylinder, and when the shielding cylinder is in an initial position, the limit block is located in the limit groove, and the limit groove limits the limit block to avoid upward and downward movement of the limit block, thereby ensuring the stability of the shielding cylinder in the initial position. Meanwhile, a moving groove is further provided on the inner wall of the needle holder, the moving groove extending along an axial direction of the needle holder. The limit groove is located on a side of an upper end of the moving groove and is communicated with the moving groove through a first guiding bevel. An end of the first guiding bevel connected to the limit groove is higher than an end of the first guiding bevel connected to the moving groove. With such an arrangement, in the process of mounting the needle holder on the insulin pen when a liquid medicine injection is required, the lower end of the shielding cylinder in the needle holder first abuts against the insulin pen, the lower end of the injection needle pierces into the pre-filled vial of the insulin pen, and as the length of the injection needle piercing into the vial increases, the shielding cylinder also moves upwardly due to the thrust given by the insulin pen; the shielding cylinder moves upwardly to drive the limit block to move upwardly, and the limit block, which is located below the first guiding bevel, moves upwardly to abut against the first guiding bevel; when the shielding cylinder continues to move upwardly, the limit block moves along the first guiding bevel to drive the shielding cylinder to rotate along the circumference of the needle holder; upon the completion of the action of mounting the needle holder on the insulin pen, the limit block finally enters the moving groove from the limit groove and remains stable up and down under the limit of the insulin pen and the limit of the top wall of the moving groove, and at this time, the liquid medicine can be driven normally by the insulin pen to complete the liquid medicine injection by means of the injection needle. Upon the completion of the liquid medicine injection, the injection needle needs to be taken off from the insulin pen, the insulin pen is separated from the shielding cylinder, the limit on downward movement of the shielding cylinder disappears, and at this time, the limit block can be driven to move downwardly along the moving groove, so as to drive the shielding cylinder to move downwardly to gradually cover the lower end of the injection needle; when the injection needle is completely removed from the insulin pen, the limit block also moves downwardly to abut against the bottom wall of the moving groove, and the shielding cylinder moves downwardly to the extreme position and completely covers and shields the lower end of the injection needle, so as to avoid a situation that a user accidentally touches the lower end of the injection needle to be injured, thereby avoiding the safety risk when the lower end of the injection needle is removed.

Optionally, the needle holder is of a hollow structure with an opening at a lower end. The shielding cylinder is slidably mounted in the needle holder through an open end of the needle holder. A spring is provided between an inner top wall of the needle holder and the shielding cylinder. The spring is in a compressed state when the limit block is located in the limit groove.

Optionally, the shielding cylinder is provided with a boss on the side wall. The boss is provided with a second guiding bevel on an upper end face. The needle holder is provided with a downwardly opening placement groove at an edge of the open end. The placement groove is provided with a third guiding bevel on an inner top wall. The second guiding bevel, the third guiding bevel and the first guiding bevel all extend along the circumference of the needle holder in a same inclination direction and at a same inclination angle. When the limit block is located in the limit groove, the boss is located below the needle holder, and after the limit block enters the moving groove from the limit groove, the boss is placed in the placement groove, and the second guiding bevel and the third guiding bevel fit against each other.

Optionally, the limit block is provided with a fourth guiding bevel on a side away from the moving groove. A fifth guiding bevel is provided at a connecting portion between the moving groove and the limit groove. A lower end of the fifth guiding bevel is closer to the moving groove as compared with an upper end. The fourth guiding bevel is parallel to the fifth guiding bevel. When the limit block moves downwardly along the moving groove and passes through the connecting portion between the moving groove and the limit groove, the fourth guiding bevel is used for abutting against the fifth guiding bevel.

Optionally, a transition groove extending along the axial direction is further provided on the inner wall of the needle holder. The transition groove is located above the moving groove and is connected to the moving groove. After the needle holder is mounted on the insulin pen, the limit block is located in the transition groove.

Optionally, the needle holder is further provided with an accommodating groove on the inner wall. A middle section of the moving groove is connected to the accommodating groove. An elastic rod is provided between the moving groove and the accommodating groove. The elastic rod is inclined towards the moving groove and is used to oscillate back and forth between the moving groove and the accommodating groove.

Optionally, a lower end of the elastic rod is arranged to be inclined towards the moving groove, and a distance between the lower end of the elastic rod and the side wall of the moving groove that is away from the accommodating groove is less than the width of the limit block.

Optionally, a mounting post is provided in the needle holder. The mounting post is disposed on an inner top wall of the needle holder. The spring and the shielding cylinder are both sleeved on the mounting post. The mounting post is used for mounting the injection needle throughout.

Optionally, the shielding apparatus for a lower end of an injection needle also includes a connecting seat, which is of a hollow structure with openings at both upper and lower ends. The needle holder and the connecting seat are connected up and down. A lower end of the shielding cylinder is located in the connecting seat. The connecting seat is provided with threads on an inner wall. The connecting seat is used for connecting with the insulin pen through the threads, such that the insulin pen abuts against the shielding cylinder and drives the shielding cylinder to move upwardly.

In another aspect, the present disclosure also provides an injection device, including an injection needle, an insulin pen, and the shielding apparatus for a lower end of an injection needle as described above.

Compared with the prior art, the beneficial effects of the injection device in the present disclosure are the same as those of the shielding apparatus for a lower end of an injection needle as described above, and will not be repeated herein.

DESCRIPTION OF REFERENCE NUMERALS

Figure 1:
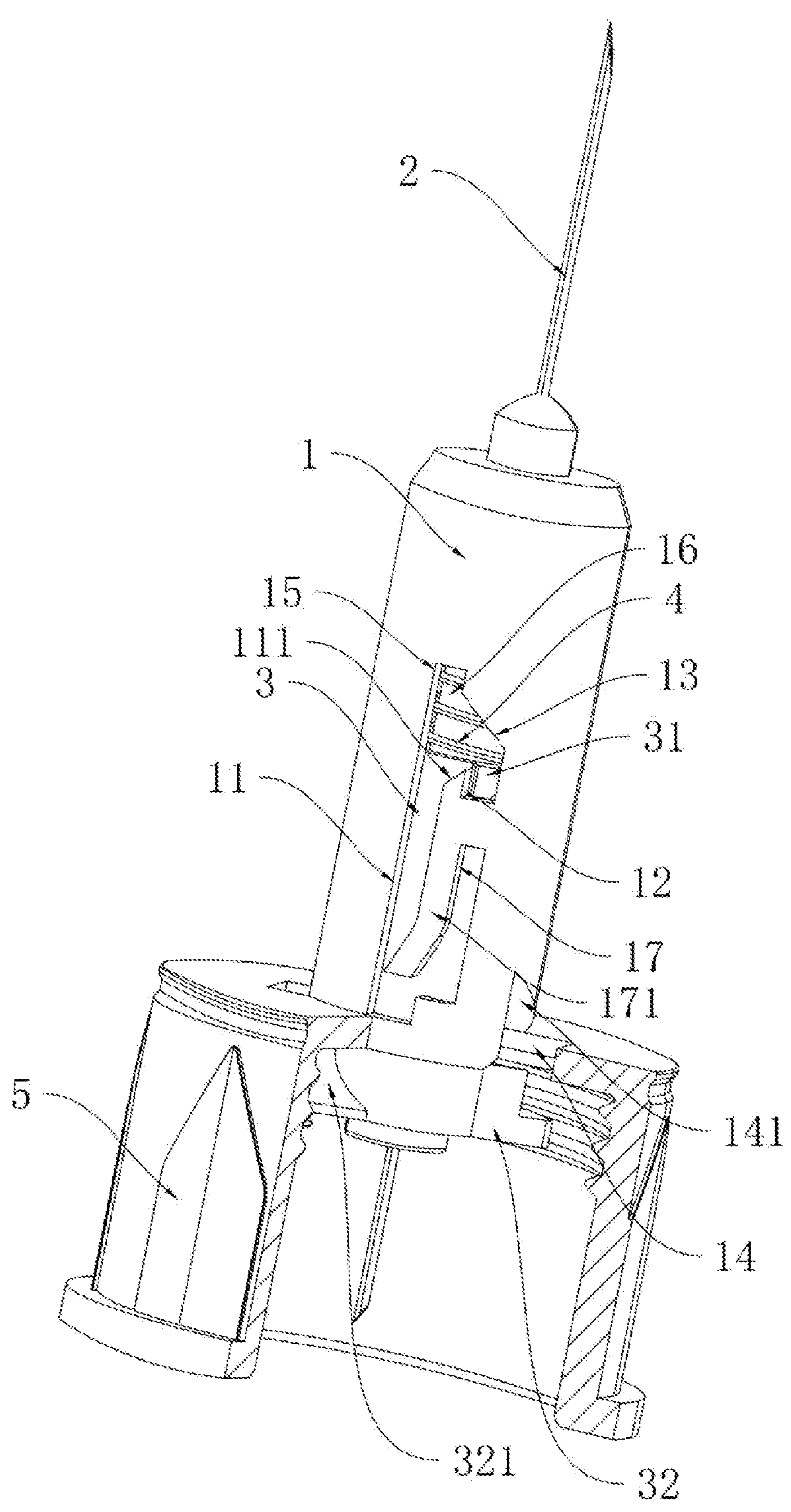
FIG. 1 is an internal schematic diagram of a shielding apparatus for a lower end of an injection needle in an embodiment of the present disclosure prior to shielding.

1—needle holder; 11—moving groove; 111—fifth guiding bevel; 12—limit groove; 13—first guiding bevel; 14—placement groove; 141—third guiding bevel; 15—transition groove; 16—mounting post; 17—accommodating groove; 171—elastic rod; 2—injection needle; 3—shielding cylinder; 31—limit block; 311—fourth guiding bevel; 32—boss; 321—second guiding bevel; 4—spring; and 5—connecting seat.

DETAILED DESCRIPTION

To make the above objects, features, and advantages of the present disclosure more obvious and understandable, the specific embodiments of the present disclosure are described in detail in conjunction with the accompanying drawings below.

It should be noted that in the coordinate system XYZ provided herein, the forward direction of the X-axis represents the right side, the reverse direction of the X-axis represents the left side, the forward direction of the Y-axis represents the front side, the reverse direction of the Y-axis represents the back side, the forward direction of the Z-axis represents the upper side, and the reverse direction of the Z-axis represents the lower side. Meanwhile, it should be noted that the terms "first", "second", etc. in the specification and claims of the present disclosure and the above accompanying drawings are used to distinguish between similar objects and need not be used to describe a particular order or sequence. It should be understood that the data so used may be interchanged, where appropriate, so that the embodiments of the present disclosure described herein can be implemented in an order other than those illustrated or described herein.

In an aspect, an embodiment of the present disclosure provides a shielding apparatus for a lower end of an injection needle, including a needle holder 1 and a shielding cylinder 3. The needle holder 1 is used for mounting of an injection needle 2 of an injection device and is mounted on an insulin pen of the injection device. The needle holder 1 is provided with a moving groove 11, a limit groove 12 and a first guiding bevel 13 on an inner wall. The moving groove 11 extends along an axial direction of the needle holder 1. The limit groove 12 is located on a side of an upper end of the moving groove 11 and is communicated with the moving groove 11 through the first guiding bevel 13. An end of the first guiding bevel 13 connected to the limit groove 12 is higher than an end of the first guiding bevel 13 connected to the moving groove 11. The shielding cylinder 3 is mounted in the needle holder 1 and allows the injection needle 2 to penetrate through. A limit block 31 for placing in the limit groove 12 is provided on a side wall of the shielding cylinder 3, and the limit block 31 is located below the first guiding bevel 13. When the needle holder 1 is mounted on the insulin pen, the shielding cylinder 3 abuts against the insulin pen and moves upwardly to allow the limit block 31 in the limit groove 12 to enter the moving groove 11 along the first guiding bevel 13. After the needle holder 1 is separated from the insulin pen, the limit block 31 moves downwardly along the moving groove 11 to allow the shielding cylinder 3 to cover and shield the lower end of the injection needle 2.

It should be noted that in the embodiment of the present disclosure, for the injection device and various structural members of the injection device, an upper end is the end that is close to the skin entry point of the human body when the injection device is used, and a lower end is the end that is far away from the skin entry point of the human body when the injection device is used.

Figure 2:
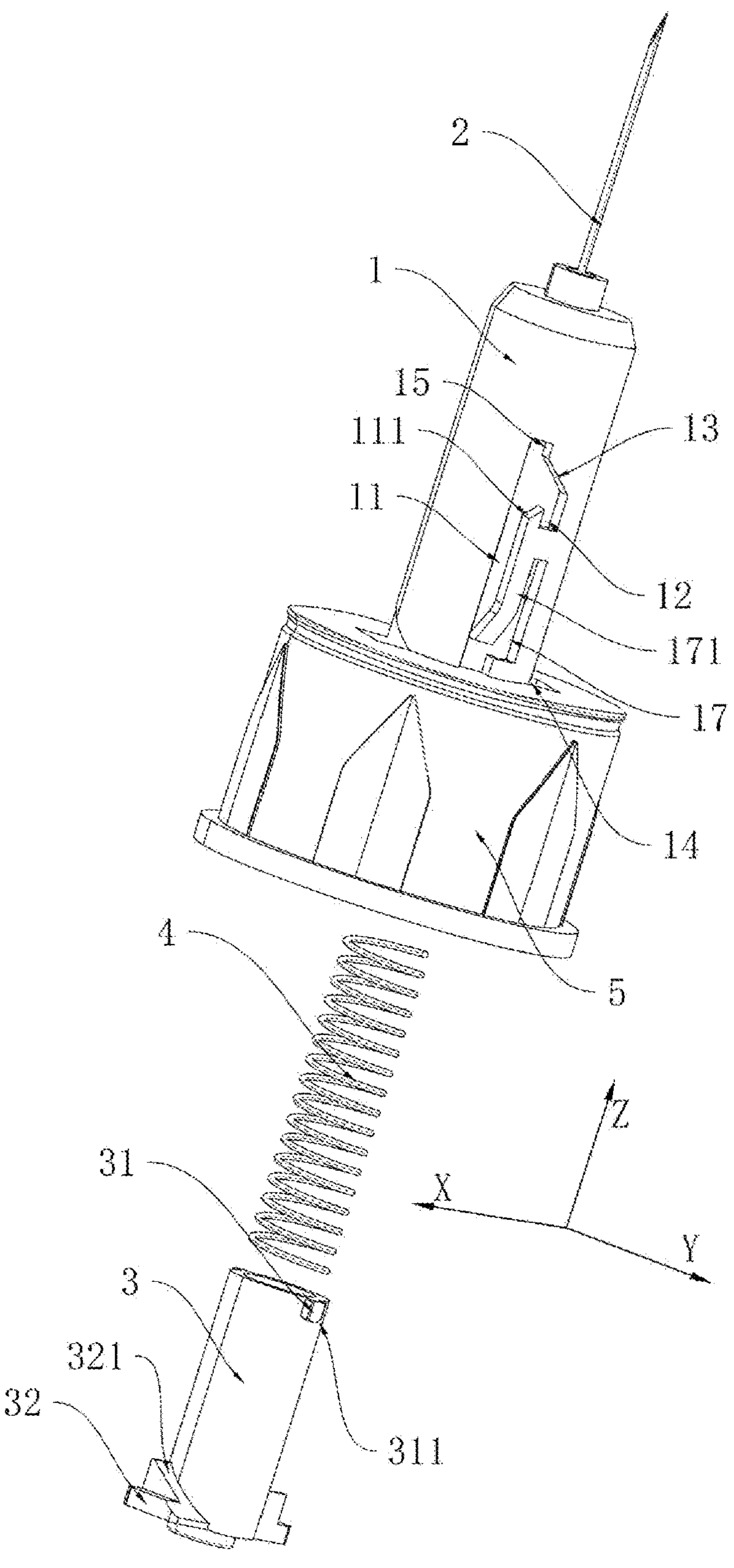
FIG. 2 is an exploded schematic diagram of the shielding apparatus for a lower end of an injection needle in an embodiment of the present disclosure.
Figure 3:
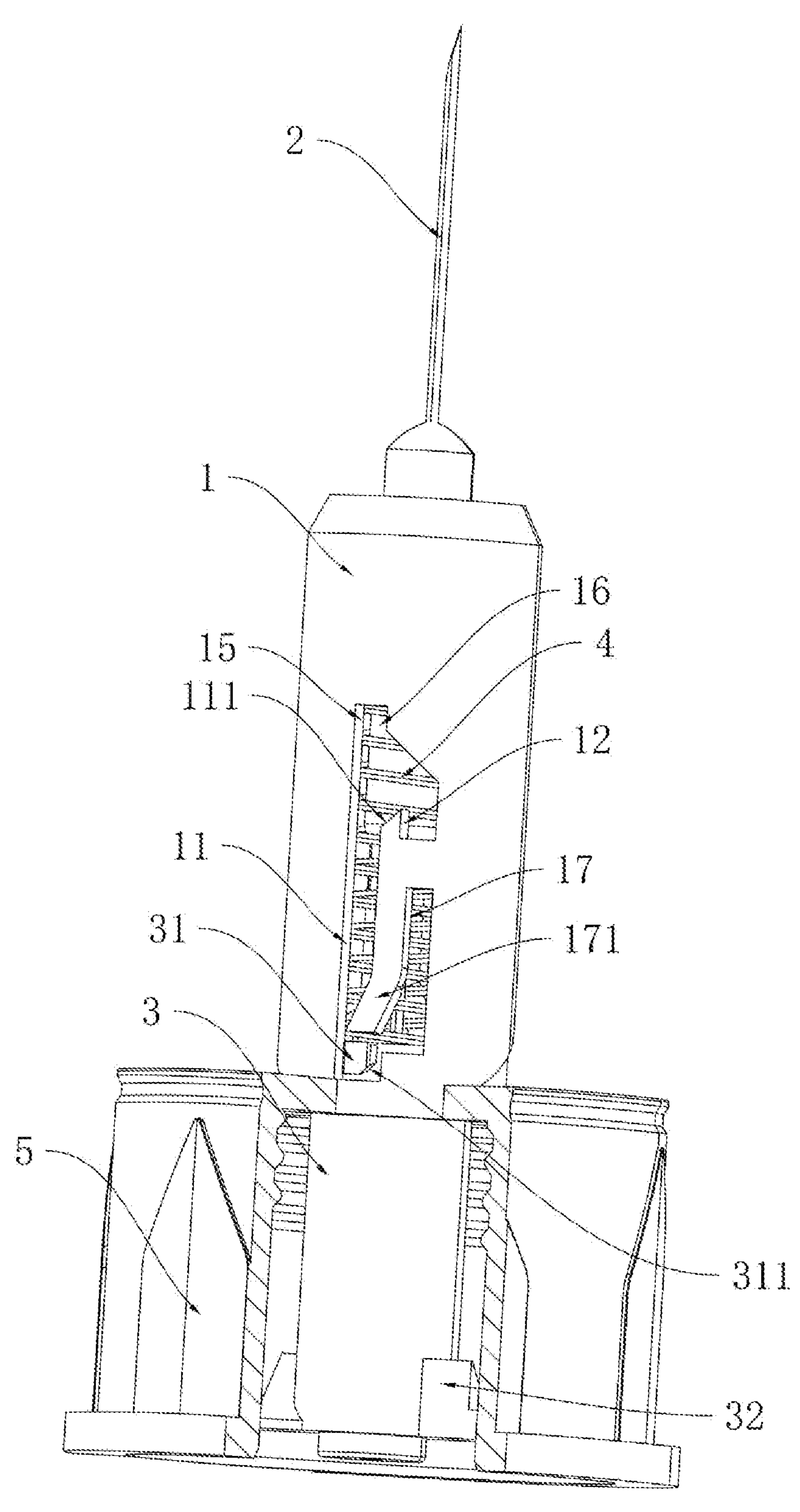
FIG. 3 is an internal schematic diagram of the shielding apparatus for a lower end of an injection needle in an embodiment of the present disclosure after shielding.

In this embodiment, as shown in FIGS. 1 and 2, a needle holder 1 is provided as a mounting structure for the injection needle 2 of the injection device. The needle holder 1 can be mounted on an insulin pen, so that the lower end of the injection needle 2 can pierce into a pre-filled vial of the insulin pen, which facilitates the completion of the injection of liquid medicine by means of the injection needle 2. Moreover, a shielding cylinder 3 is mounted in the needle holder 1, which allows the injection needle 2 to penetrate through, so as to prevent interference caused by the mounting and normal use of the injection needle 2. On this basis, a limit groove 12 is provided on an inner wall of the needle holder 1, and a limit block 31 is provided on a side wall of the shielding cylinder 3. When the shielding cylinder 3 is in an initial position, the limit block 31 is located in the limit groove 12, and the limit groove 12 limits the limit block 31 to avoid upward and downward movement of the limit block 31, thereby ensuring the stability of the shielding cylinder 3 in the initial position. Meanwhile, a moving groove 11 is further provided on the inner wall of the needle holder 1, and the moving groove 11 extends along an axial direction of the needle holder 1. The limit groove 12 is located on a side of an upper end of the moving groove 11 and is communicated with the moving groove 11 through a first guiding bevel 13. An end of the first guiding bevel 13 connected to the limit groove 12 is higher than an end of the first guiding bevel 13 connected to the moving groove 11, and the limit block 31 is located below the first guiding bevel 13. With such an arrangement, in the process of mounting the needle holder 1 on the insulin pen when a liquid medicine injection is required, the lower end of the shielding cylinder 3 in the needle holder 1 first abuts against the insulin pen, the lower end of the injection needle 2 pierces into the pre-filled vial of the insulin pen, and as the length of the injection needle 2 piercing into the vial increases, the shielding cylinder 3 also moves upwardly due to the thrust given by the insulin pen; the shielding cylinder 3 moves upwardly to drive the limit block 31 to move upwardly, and the limit block 31, which is located below the first guiding bevel 13, moves upwardly to abut against the first guiding bevel 13; when the shielding cylinder 3 continues to move upwardly, the limit block 31 moves along the first guiding bevel 13 to drive the shielding cylinder 3 to rotate along the circumference of the needle holder 1; upon the completion of the action of mounting the needle holder 1 on the insulin pen, the limit block 31 finally enters the moving groove 11 from the limit groove 12 and remains stable up and down under the limit of the insulin pen and the limit of a top wall of the moving groove 11, and at this time, the liquid medicine can be driven normally by the insulin pen to complete the liquid medicine injection by means of the injection needle 2. Upon the completion of the liquid medicine injection, the injection needle 2 needs to be taken off from the insulin pen, the insulin pen is separated from the shielding cylinder 3, the limit on downward movement of the shielding cylinder 3 disappears, and at this time, the limit block 31 can be driven to move downwardly along the moving groove 11, so as to drive the shielding cylinder 3 to move downwardly to gradually cover the lower end of the injection needle 2; when the injection needle 2 is completely removed from the insulin pen, as shown in FIG. 3, the limit block 31 also moves downwardly to abut against the bottom wall of the moving groove 11, and the shielding cylinder 3 moves downwardly to the extreme position and completely covers and shields the lower end of the injection needle 2, so as to avoid a situation that a user accidentally touches the lower end of the injection needle 2 to be injured, thereby avoiding the safety risk when the lower end of the injection needle is removed.

Optionally, the needle holder 1 is of a hollow structure with an opening at the lower end. The shielding cylinder 3 is slidably mounted in the needle holder 1 through an open end of the needle holder 1. A spring 4 is provided between an inner top wall of the needle holder 1 and the shielding cylinder 3. The spring 4 is in a compressed state when the limit block 31 is located in the limit groove 12.

In order to enhance the stability of the shielding cylinder 3 when covering and shielding the lower end of the injection needle 2, in this embodiment, as shown in FIGS. 1 and 2, the needle holder 1 is arranged to be a hollow structure with an opening at the lower end, the shielding cylinder 3 can be slidably mounted in the needle holder 1 through the open end of the needle holder 1, and a spring 4 is provided between the inner top wall of the needle holder 1 and the shielding cylinder 3, so that the spring 4 is in a compressed state when the limit block 31 is located in the limit groove 12, that is, the shielding cylinder 3 is in an initial position. By such an arrangement, when the needle holder 1 is mounted on the insulin pen, that is, when the lower end of the injection needle 2 pierces into a vial of the insulin pen which is pre-filled with a liquid medicine, the insulin pen abuts against the lower end of the shielding cylinder 3 to drive the shielding cylinder 3 to move upwardly, the spring 4 is further compressed, and at the same time, the limit block 31 enters the moving groove 11 from the limit groove 12. Upon the completion of the injection, the injection needle 2 is pulled out from the insulin pen, the pressure on the spring 4 disappears, so the spring 4 is stretched out, and due to the support function of the inner top wall of the needle holder 1, the spring 4 gives the shielding cylinder 3 an elastic driving force to drive the shielding cylinder 3 to move downwardly to cover and shield the lower end of the injection needle 2. In this process, the limit block 31 moves synchronously along the moving groove 11. As shown in FIG. 3, when the limit block 31 abuts against the bottom wall of the moving groove 11, it is indicated that the shielding cylinder 3 has covered and shielded the lower end of the injection needle 2, and due to the limit of the limit block 31 by the bottom wall of the moving groove 11, the shielding cylinder 3 will not continue to move downwardly to be separated from the needle holder 1, which ensures the stability of the shielding cylinder 3 when covering and shielding the lower end of the injection needle 2. In addition, after the shielding cylinder 3 covers and shields the lower end of the injection needle 2, the spring 4 may also be in a compressed state to continue to provide downward pressure for the shielding cylinder 3, so as to avoid a situation that a user accidentally touches the shielding cylinder 3 to give it an upward thrust to expose the lower end of the injection needle 2 and thus gets injured, thereby further avoiding the safety risk when the lower end of the injection needle is removed.

Optionally, the shielding cylinder 3 is provided with a boss 32 on the side wall. The boss 32 is provided with a second guiding bevel 321 on an upper end face. The needle holder 1 is provided with a downwardly opening placement groove 14 at an edge of the open end. The placement groove 14 is provided with a third guiding bevel 141 on an inner top wall. The second guiding bevel 321, the third guiding bevel 141 and the first guiding bevel 13 all extend along the circumference of the needle holder 1 in a same inclination direction and at a same inclination angle. When the limit block 31 is located in the limit groove 12, the boss 32 is located below the needle holder 1, and after the limit block 31 enters the moving groove 11 from the limit groove 12, the boss 32 is placed in the placement groove 14, and the second guiding bevel 321 and the third guiding bevel 141 fit against each other.

In order to ensure the stability of the shielding cylinder 3 during upward movement, in this embodiment, as shown in FIGS. 1 and 2, the shielding cylinder 3 is provided with a boss 32 on the side wall, the boss 32 is provided with a second guiding bevel 321, the needle holder 1 is provided with a downwardly opening placement groove 14 at an edge of the open end, and the placement groove 14 is provided with a third guiding bevel 141 on an inner top wall. The second guiding bevel 321, the third guiding bevel 141 and the first guiding bevel 13 all extend along the circumference of the needle holder 1 in a same inclination direction and at a same inclination angle. When the limit block 31 is located in the limit groove 12, the boss 32 is located below the needle holder 1, while after the limit block 31 enters the moving groove 11 from the limit groove 12, the boss 32 is placed in the placement groove 14, and the second guiding bevel 321 and the third guiding bevel 141 fit against each other. With such an arrangement, when the shielding cylinder 3 moves upwardly due to the thrust given by the insulin pen, the boss 32 will move upwardly along with the shielding cylinder 3 and approach the placement groove 14. The limit block 31 will also move along the first guiding bevel 13 while the shielding cylinder 3 moves upwardly, so as to drive the shielding cylinder 3 to rotate. The rotation of the shielding cylinder 3 will drive the boss 32 to move along the circumference of the shielding cylinder 3, such that the upper end of the second guiding bevel 321 on the boss 32 is in contact against the lower end of the third guiding bevel 141 of the placement groove 14. With the rotation of the shielding cylinder 3, the area of contact between the second guiding bevel 321 and the third guiding bevel 141 increases, and the boss 32 can enter the placement groove 14 along the third guiding bevel 141, such that the stability of the shielding cylinder 3 when moving upwardly and rotating is ensured. After the limit block 31 enters the moving groove 11 from the limit groove 12, the shielding cylinder 3 stops moving upwardly, while the boss 32 is placed in the placement groove 14, and the second guiding bevel 321 and the third guiding bevel 141 fit against each other.

It should be noted that in this embodiment, as shown in FIG. 2, the bottom wall of the boss 32 is flush with the bottom wall of the shielding cylinder 3, and when the shielding cylinder 3 abuts against the insulin pen, the boss 32 also abuts against the insulin pen, so that the overall area of contact between the shielding cylinder 3 and the insulin pen when the shielding cylinder 3 moves is increased, thereby improving the stability of upward movement.

Optionally, the limit block 31 is provided with a fourth guiding bevel 311 on a side away from the moving groove 11. A fifth guiding bevel 111 is provided at a connecting portion between the moving groove 11 and the limit groove 12. A lower end of the fifth guiding bevel 111 is closer to the moving groove 11 as compared with an upper end. The fourth guiding bevel 311 is parallel to the fifth guiding bevel 111. When the limit block 31 moves downwardly along the moving groove 11 and passes through the connecting portion between the moving groove 11 and the limit groove 12, the fourth guiding bevel 311 is used for abutting against the fifth guiding bevel 111.

To prevent the limit block 31 from entering the limit groove 12 when moving downwardly, in this embodiment, as shown in FIGS. 1 and 2, the limit block 31 is provided with a fourth guiding bevel 311 on a side away from the moving groove 11, and a fifth guiding bevel 111 is provided at a connecting portion between the moving groove 11 and the limit groove 12. A lower end of the fifth guiding bevel 111 is closer to the moving groove 11 as compared with an upper end, and the fourth guiding bevel 311 is parallel to the fifth guiding bevel 111. When the limit block 31 moves downwardly along the moving groove 11 and passes through the connecting portion between the moving groove 11 and the limit groove 12, the fourth guiding bevel 311 is used for abutting against the fifth guiding bevel 111. With such an arrangement, when the shielding cylinder 3 moves downwardly, the limit block 31 moves downwardly along the moving groove 11, and when passing through the connecting portion between the moving groove 11 and the limit groove 12, the fourth guiding bevel 311 is used for abutting against the fifth guiding bevel 111. The force that urges the limit block 31 to move downwardly acts on the fifth guiding bevel 111 and is divided into a component force along the fifth guiding bevel 111 and a component force perpendicular to the fifth guiding bevel 111. The component force along the fifth guiding bevel 111 is tilted downwardly from the limit groove 12 to direct to the moving groove 11, and under the action of such a component force, the limit block 31 maintains a stable movement in the moving groove 11 without entering the limit groove 12. Furthermore, the fourth guiding bevel 311 is slidable with respect to the fifth guiding bevel 111, so as to ensure the stability of the movement of the limit block 31 along the fifth guiding bevel 111.

Optionally, a transition groove 15 that extends along the axial direction is also provided on the inner wall of the needle holder 1. The transition groove 15 is located above the moving groove 11 and is connected to the moving groove 11. After the needle holder 1 is mounted on the insulin pen, the limit block 31 is located in the transition groove 15.

In this embodiment, as shown in FIGS. 1 to 3, a transition groove 15 that extends along the axial direction is also provided on the inner wall of the needle holder 1. The transition groove 15 is located above the moving groove 11 and is connected to the moving groove 11, and after the needle holder 1 is mounted on the insulin pen, the limit block 31 is located in the transition groove 15. With such an arrangement, after the shielding cylinder 3 moves upwardly due to the thrust and drives the limit block 31 to enter the moving groove 11 from the limit groove 12, the shielding cylinder 3 continues to move upwardly so that the limit block 31 enters the transition groove 15. The transition groove 15 extends along the axial direction of the needle holder 1. When the needle holder 1 is removed from the insulin pen, the opposing side walls of the transition groove 15 can provide limit for the limit block 31, so that the limit block 31 maintains a vertical downward movement to provide a certain initial velocity, and then stably enters the moving groove 11, thereby further avoiding an offset in the downward movement of the limit block 31 that would result in the shielding cylinder 3 not being able to completely cover and shield the lower end of the injection needle 2.

Optionally, the needle holder 1 is further provided with an accommodating groove 17 on the inner wall. A middle section of the moving groove 11 is connected to the accommodating groove 17. An elastic rod 171 is provided between the moving groove 11 and the accommodating groove 17. The elastic rod 171 is inclined towards the moving groove 11 and is used to oscillate back and forth between the moving groove 11 and the accommodating groove 17.

In this embodiment, as shown in FIGS. 1 and 3, the needle holder 1 is provided with an accommodating groove 17 on the inner wall, the accommodating groove 17 is located below the limit groove 12, an elastic rod 171 is provided between the moving groove 11 and the accommodating groove 17, and the elastic rod 171 is inclined towards the moving groove 11 and is used to oscillate back and forth between the moving groove 11 and the accommodating groove 17. With such an arrangement, when the limit block 31 moves downwardly along the moving groove 11, as the elastic rod 171 is inclined toward the moving groove 11, the limit block 31 will squeeze one side of the elastic rod 171 toward the accommodating groove 17 so that the elastic rod 171 oscillates toward the accommodating groove 17, and the limit block 31 can continue to move downwardly. After the limit block 31 passes through, the squeezing force on the elastic rod 171 disappears, and the elastic rod 171 resets. At this time, if the shielding cylinder 3 is subjected to an upward thrust, the limit block 31 will abut against the other side of the elastic rod 171, so as to squeeze the elastic rod 171 in the direction away from the accommodating groove 17. With respect to the elastic rod 171, a side wall of the moving groove 11 is located on the opposite side of the accommodating groove 17, and the side wall of the moving groove 11 will cause a limit on the oscillation of the elastic rod 171, so that the limit block 31 cannot move upwardly, thereby avoiding a situation that a user accidentally touches the shielding cylinder 3 to give it an upward thrust to expose the lower end of the injection needle 2 and thus gets injured, thereby further avoiding the safety risk when the lower end of the injection needle is removed.

Optionally, a lower end of the elastic rod 171 is arranged to be inclined towards the moving groove 11, and a distance between the lower end of the elastic rod 171 and the side wall of the moving groove 11 that is away from the accommodating groove 17 is less than the width of the limit block 31.

In this embodiment, as shown in FIGS. 1 and 2, a lower end of the elastic rod 171 is arranged to be inclined towards the moving groove 11, and a distance between the lower end of the elastic rod 171 and the side wall of the moving groove 11 that is away from the accommodating groove 17 is less than the width of the limit block 31. With such an arrangement, as the lower end of the elastic rod 171 is inclined toward the moving groove 11, when moving downwardly along the moving groove 11, the limit block 31 will squeeze a side of the lower end of the elastic rod 171 toward the accommodating groove 17 so that the elastic rod 171 oscillates toward the accommodating groove 17, and the limit block 31 can continue to move downwardly. After the limit block 31 passes through, the squeezing force on the lower end of the elastic rod 171 disappears, and the elastic rod 171 resets. At this time, if the shielding cylinder 3 is subjected to an upward thrust, the limit block 31 will abut against the other side of the elastic rod 171, so as to squeeze the lower end of the elastic rod 171 in the direction away from the accommodating groove 17. With respect to the lower end of the elastic rod 171, a side wall of the moving groove 11 is located on the opposite side of the accommodating groove 17, and the side wall of the moving groove 11 will cause a limit on the oscillation of the lower end of the elastic rod 171, so that the limit block 31 cannot move upwardly, thereby avoiding a situation that a user accidentally touches the shielding cylinder 3 to give it an upward thrust to expose the lower end of the injection needle 2, and thus gets injured, thereby further avoiding the safety risk when the lower end of the injection needle is removed.

Optionally, a mounting post 16 is provided in the needle holder 1. The mounting post 16 is disposed on an inner top wall of the needle holder 1. The spring 4 and the shielding cylinder 3 are both sleeved on the mounting post 16. The mounting post 16 is used for mounting the injection needle 2 throughout.

To ensure the stability of the installation and movement of the spring 4 and the shielding cylinder 3, in this embodiment, as shown in FIGS. 1 to 3, a mounting post 16 is provided in the needle holder 1 on an inner top wall of the needle holder 1 and can be used for mounting the injection needle 2 throughout, ensuring the stability of the installation of the injection needle 2. On this basis, the spring 4 and the shielding cylinder 3 can both be sleeved on the mounting post 16 to improve the stability of the installation of the spring 4 and the shielding cylinder 3. Furthermore, the mounting post 16 can guide the expansion and contraction of the spring 4 and the movement of the shielding cylinder 3, so as to ensure the stability of the movement of the spring 4 and the shielding cylinder 3.

Optionally, the shielding apparatus for a lower end of an injection needle further includes a connecting seat 5. The connecting seat 5 is of a hollow structure with openings at both upper and lower ends. The needle holder 1 and the connecting seat 5 are connected up and down. A lower end of the shielding cylinder 3 is located in the connecting seat 5. The connecting seat 5 is provided with threads on an inner wall. The connecting seat 5 is used for connecting with the insulin pen through the threads, such that the insulin pen abuts against the shielding cylinder 3 and drives the shielding cylinder 3 to move upwardly.

To improve the stability of the connection between the needle holder 1 and the insulin pen, in this embodiment, as shown in FIGS. 1 to 3, a connecting seat 5 is further provided, which is of a hollow structure with openings at both upper and lower ends. The needle holder 1 and the connecting seat 5 are connected up and down. The connecting seat 5 is provided with threads on an inner wall and is used for connecting with the insulin pen through the threads. With such an arrangement, the upper end of the insulin pen can be rotated into the connecting seat 5 to improve the stability of the connection between the needle holder 1 and the insulin pen, and the lower end of the injection needle 2 in the needle holder 1 pierces into the vial while the insulin pen rotates and moves upwardly. On this basis, the lower end of the shielding cylinder 3 is located in the connecting seat 5. With such an arrangement, the insulin pen can abut against the lower end of the shielding cylinder 3 while rotating and moving upwardly to be mounted in the connecting seat 5, thereby driving the shielding cylinder 3 to move upwardly.

In another aspect, an embodiment of the present disclosure provides an injection device, including an injection needle 2, an insulin pen, and the shielding apparatus for a lower end of an injection needle as described above.

As shown in FIGS. 1 to 3, the technical effects of the injection device in this embodiment are similar to those of the shielding apparatus for the lower end of the injection needle as described above, and will not be repeated herein.

Although the present disclosure is disclosed as above, the scope of protection of the present disclosure is not limited thereto. Various changes and modifications can be made by those skilled in the art without departing from the spirit and scope of the present disclosure, and will all fall within the scope of protection of the present disclosure.

What is claimed is:

1. A shielding apparatus for a lower end of an injection needle, comprising:

a needle holder (1), used for mounting of an injection needle (2) of an injection device and mounted on an insulin pen of the injection device, wherein the needle holder (1) is provided with a moving groove (11), a limit groove (12) and a first guiding bevel (13) on an inner wall, the moving groove (11) extending along an axial direction of the needle holder (1), the limit groove (12) being located on a side of an upper end of the moving groove (11) and being communicated with the moving groove (11) through the first guiding bevel (13), and an end of the first guiding bevel (13) connected to the limit groove (12) being higher than an end of the first guiding bevel (13) connected to the moving groove (11); and a shielding cylinder (3), mounted in the needle holder (1) and allowing the injection needle (2) to penetrate through, wherein a limit block (31) for placing in the limit groove (12) is provided on a side wall of the shielding cylinder (3), the limit block (31) being located below the first guiding bevel (13); when the needle holder (1) is mounted on the insulin pen, the shielding cylinder (3) abuts against the insulin pen and moves upwardly to allow the limit block (31) in the limit groove (12) to enter the moving groove (11) along the first guiding bevel (13); and after the needle holder (1) is separated from the insulin pen, the limit block (31) moves downwardly along the moving groove (11) to allow the shielding cylinder (3) to cover and shield the lower end of the injection needle (2).

2. The shielding apparatus for a lower end of an injection needle of claim 1, wherein the needle holder (1) is of a hollow structure with an opening at a lower end, the shielding cylinder (3) is slidably mounted in the needle holder (1) through an open end of the needle holder (1), a spring (4) is provided between an inner top wall of the needle holder (1) and the shielding cylinder (3), and the spring (4) is in a compressed state when the limit block (31) is located in the limit groove (12).

3. The shielding apparatus for a lower end of an injection needle of claim 2, wherein the shielding cylinder (3) is provided with a boss (32) on the side wall, and the boss (32) is provided with a second guiding bevel (321) on an upper end face; the needle holder (1) is provided with a downwardly opening placement groove (14) at an edge of the open end, and the placement groove (14) is provided with a third guiding bevel (141) on an inner top wall; the second guiding bevel (321), the third guiding bevel (141) and the first guiding bevel (13) all extend along the circumference of the needle holder (1) in a same inclination direction and at a same inclination angle; when the limit block (31) is located in the limit groove (12), the boss (32) is located below the needle holder (1), and after the limit block (31) enters the moving groove (11) from the limit groove (12), the boss (32) is placed in the placement groove (14), and the second guiding bevel (321) and the third guiding bevel (141) fit against each other.

4. The shielding apparatus for a lower end of an injection needle of claim 2, wherein the limit block (31) is provided with a fourth guiding bevel (311) on a side away from the moving groove (11), a fifth guiding bevel (111) is provided at a connecting portion between the moving groove (11) and the limit groove (12), a lower end of the fifth guiding bevel (111) is closer to the moving groove (11) as compared with an upper end, the fourth guiding bevel (311) is parallel to the fifth guiding bevel (111), and when the limit block (31) moves downwardly along the moving groove (11) and passes through the connecting portion between the moving groove (11) and the limit groove (12), the fourth guiding bevel (311) is used for abutting against the fifth guiding bevel (111).

5. The shielding apparatus for a lower end of an injection needle of claim 4, wherein a transition groove (15) extending along the axial direction is further provided on the inner wall of the needle holder (1), the transition groove (15) is located above the moving groove (11) and is connected to the moving groove (11), and after the needle holder (1) is mounted on the insulin pen, the limit block (31) is located in the transition groove (15).

6. The shielding apparatus for a lower end of the injection needle of claim 2, wherein the needle holder (1) is further provided with an accommodating groove (17) on the inner wall, a middle section of the moving groove (11) is connected to the accommodating groove (17), an elastic rod (171) is provided between the moving groove (11) and the accommodating groove (17), and the elastic rod (171) is inclined towards the moving groove (11) and is used to oscillate back and forth between the moving groove (11) and the accommodating groove (17).

7. The shielding apparatus for a lower end of an injection needle of claim 6, wherein a lower end of the elastic rod (171) is arranged to be inclined towards the moving groove (11), and a distance between the lower end of the elastic rod (171) and a side wall of the moving groove (11) away from the accommodating groove (17) is less than the width of the limit block (31).

8. The shielding apparatus for a lower end of an injection needle of any one of claims 2 to 7, wherein a mounting post (16) is provided in the needle holder (1), the mounting post (16) is disposed on an inner top wall of the needle holder (1), the spring (4) and the shielding cylinder (3) are both sleeved on the mounting post (16), and the mounting post (16) is used for mounting the injection needle (2) throughout.

9. The shielding apparatus for a lower end of an injection needle of any one of claims 2 to 7, further comprising a connecting seat (5), which is of a hollow structure with openings at both an upper end and a lower end, wherein the needle holder (1) and the connecting seat (5) are connected up and down, a lower end of the shielding cylinder (3) is located in the connecting seat (5), the connecting seat (5) is provided with threads on an inner wall, and the connecting seat (5) is used for connecting with the insulin pen through the threads, such that the insulin pen abuts against the shielding cylinder (3) and drives the shielding cylinder (3) to move upwardly.

10. An injection device, comprising an injection needle (2), an insulin pen, and the shielding apparatus for a lower end of an injection needle of claim 1.

* * * * *